United States Patent [19]
Baumgardner et al.

[11] Patent Number: 6,133,567
[45] Date of Patent: *Oct. 17, 2000

[54] PROBE FOR THE MEASUREMENT OF GAS TENSIONS

[75] Inventors: James E. Baumgardner, Folsom, Pa.; Gordon R. Neufeld, Shiprock, N. Mex.; Bryan E. Marshall, Philadelphia, Pa.

[73] Assignee: The Trustees of the University of Pennsylvania, Philadelphia, Pa.

[ * ] Notice: This patent is subject to a terminal disclaimer.

[21] Appl. No.: 09/167,562

[22] Filed: Oct. 7, 1998

Related U.S. Application Data

[63] Continuation-in-part of application No. 08/540,688, Oct. 11, 1995, Pat. No. 5,834,772, which is a continuation of application No. 08/416,018, Apr. 3, 1995, abandoned, which is a continuation of application No. 08/311,218, Sep. 23, 1994, abandoned.

[51] Int. Cl.$^7$ .................................................. B01D 59/44
[52] U.S. Cl. ............................................................ 250/288
[58] Field of Search .................................. 250/288, 288 A, 250/281, 282, 423 R

[56] References Cited

U.S. PATENT DOCUMENTS

| | | | |
|---|---|---|---|
| 3,867,631 | 2/1975 | Briggs et al. ............................ | 250/288 |
| 5,834,772 | 11/1998 | Baumgardner et al. ................. | 250/288 |

*Primary Examiner*—Kiet T. Nguyen
*Attorney, Agent, or Firm*—Pennie & Edmonds LLP

[57] ABSTRACT

A gas measurement probe for measuring gas tensions in liquid. The probe comprises a tubing having one end adapted for connection to a gas measurement device, such as a mass spectrometer, a gas chromatograph, an infrared spectrometer or a Raman spectrometer, among others. The second end of the probe is provided with a tip having at least one pore formed in it. The pore is filled with a membrane material which eliminates water from entering, but admits low molecular weight gases. These low molecular weight gases may then be identified by the measurement device.

19 Claims, 9 Drawing Sheets

PROBE FOR THE MEASUREMENT OF GAS TENSIONS

RELATED APPLICATIONS

This is a continuation-in-part of U.S. application Ser. No. 08/540,688, filed Oct. 11, 1995, now U.S. Pat. No. 5,834,772, which was a continuation of Ser. No. 08/416,018, filed Apr. 3, 1995, now abandoned, which was a continuation of Ser. No. 08/311,218, filed Sep. 23, 1994, now abandoned.

FIELD OF THE INVENTION

The present invention is directed to probes for the measurement of gas tensions. In particular, the present invention is directed to a probe for measuring gas tensions such as in blood and saline, which may be coupled to a measurement device such as a mass spectrometer, gas chromatograph, infrared spectrometers, Raman spectrometers, and the like.

BACKGROUND OF THE INVENTION

The present invention is directed to mass spectrometer probes for measuring gas tensions. Mechanisms of tissue oxygenation are complex and are not completely understood. The experimental study of the interaction of blood flow, diffusion and metabolism require measurements of gas tensions with a high decree of spatial resolution. Capillary diameters typically range from 6 to 8 microns, which limit spatial resolution.

Oxygen microelectrodes have been used in two ways to measure tissue partial pressure of oxygen ($TPO_2$) with micron range resolution: as a single electrode within a micropipette, driven into tissue with a micromanipulator; or as a flat array of multiple microelectrodes for the simultaneous measurement of several oxygen tensions at the tissue surface.

Mass spectrometry provides a number of advantages over electrode techniques for the study of tissue gas exchange, including an inherent ability to measure a variety of gases and providing exceptional sensitivity. In addition to measurements of $TPO_2$, mass spectrometers can measure partial pressures of $CO_2$ as well as several tracer gases introduced for the study of transport mechanisms. Measurements of tissue gas exchange for a series of gases with a spectrum of physical properties are useful for determining the dependence of transport on tissue and blood solubility, diffusivity and metabolism.

Membrane inlet mass spectrometry (MIMS) has been used to measure gas tensions in aqueous solutions, in both blood and tissue. No currently available MIMS system, however, can provide spatial resolution adequate for studies of gas tensions on a micron scale. The selected introduction of gas components of a fluid into a mass spectrometer has been a long-standing problem.

The prior art has disclosed two types of technologies for measuring liquid phase gas tensions. First, membrane inlet systems have been designed for use in mass spectrometers in which a gas sample is introduced into the mass spectrometer by diffusion through a membrane. These systems typically use a large surface area for the membrane (one square centimeter), which requires a large blood sample to make measurements, and which limits spatial resolution.

MIMS provide the ability to quantify a wide variety of gaseous and volatile species simultaneously. This general property of mass spectrometry contrasts sharply with electrochemical analytic approaches, which are typically restricted to the measurement of only one or two reactive species. Specifically, polarographic microelectrodes have been used to quantify tissue oxygen tension as well as tissue hydrogen clearance. They cannot measure tensions of other gases of interest.

Mass spectrometer techniques excel for the measurement of multiple species, including inert gases that are used as tracers in studies of gas exchange. There are some restrictions on the nature of molecules that can be examined with membrane inlet systems. MIMS is most suitable for use with low molecular weight, nonpolar molecules.

With such systems, the limited spatial resolution makes it impossible to measure gas tension gradients, an important factor in some research applications. The larger surface area required for mechanical stability substantially limits the time response. In addition, many of the membrane inlet systems that have been reported use a much higher gas sampling rate which leads to diffusional limitations in the liquid phase thereby making the device impossible to calibrate in situ. Membrane-covered electrodes have been very useful for physiological measurements of the partial pressures of certain gases in the liquid phase. These electrodes are available commercially for $O_2$, $CO_2$ and $H_2$. Electrodes can be made very small at the probe tip thereby permitting an excellent spatial resolution.

Unfortunately, electrode approaches have two intrinsic limitations. First, they require a large gas sample rate. Secondly, only certain reactive gas species can be measured. Mass spectrometers are intrinsically able to measure gas tensions with a smaller gas sample rate than are electrodes. At present, all previous electrodes for $O_2$ and $CO_2$ have required a large enough gas sample to induce stirring, thereby making in situ calibration difficult. Further, membrane-covered electrodes can only measure reactive species and not gases that are physiologically inert.

The prior art patent literature has disclosed several technologies using membrane and capillary-based technologies for facilitating gas tension measurement. U.S. Pat. No. 5,306,412, for example, teaches the use of mechanical vibration to enhance the electrostatic dispersion of sample solutions into the small, highly charged droplets that can produce ions of solute species for mass spectrometric analysis. The vibration is effective at ultrasonic frequencies for solutions with flow rates, conductivities and surface tensions too high for stable dispersion by electrostatic forces alone as in conventional electrospray ionization.

U.S. Pat. No. 4,439,679 discloses a device for the measurement of the tension of blood gases and resistance of the skin to the flow of such gases. The invention comprises a body having a gas permeable boundary comprising two gas permeable membranes for placement on the skin of the subject, two gas collection chambers in the body connected to a gas analysis system, a heating device to heat the skin area under the boundary and control means operable to control the heating device.

U.S. Pat. No. 4,791,292 discloses a capillary membrane interface for a mass spectrometer. The probe includes conduit passageways for permitting bi-directional fluid flow through diffusion in the capillary. See also U.S. Pat. No. 5,078,135.

Each of the above devices has a number of deficiencies. There has been a long-felt need for a single membrane probe for use in conjunction with mass spectrometers which exclude water and polar compounds which provide extremely low gas sample rates using a novel pore structure. Such a probe could be utilized to measure gas tensions of gases found in blood and saline such as $O_2$, $CO_2$, He and Xenon. Such a membrane could provide no stirring effect, a high spatial resolution and rapid response speed. The prior art systems provide either no stirring effect or a rapid response time but not a combination of the two.

Also, prior systems have used a high gas sample rate which induced diffusional resistance in the liquid layers surrounding the membrane. The measurement system signal then depended partly on the amount of stirring of the liquid, as well as protein deposits on the membrane, neither of which could be controlled during the measurement. The calibration performed in vitro therefore could not apply to the probe during the measurements, and there was no accurate way to calibrate the system in situ.

SUMMARY OF THE INVENTION

The present invention is directed to a membrane inlet system for use with a measurement device which excludes water and polar compounds, while admitting gases for analysis. The present invention can thus be used to measure gas tensions of oxygen, carbon dioxide, helium, argon, nitrous oxide and many other gases and volatile species in aqueous solutions (including blood and saline) which are prepared for calibration of the probe.

In accordance with the present invention, a gas measurement probe for measurement of gas tensions of such liquids as blood and saline is disclosed. The probe is intended for use with a gas phase measurement device capable of measuring a partial pressure of components of a carrier gas. Such devices can include mass spectrometers, gas chromatographs, infrared (IR) spectrometers, and Raman spectrometers, among other.

The probe of the invention comprises a tubing having one end adapted for connection to the gas measurement device, and a second end defined as a sealed probe tip and having at least one pore extending therethrough. The pore is at least partially filled with a membrane formed of a material that prevents water from entering the tubing, but permits low molecular weight gases to enter the tubing.

In one aspect of the invention, the probe comprises a steel tubing comprising a shaped welded tip at one end and adapted at a second end to a vacuum fitting for connection to the measurement device.

In another aspect of the invention, the probe comprises a stainless steel tubing provided with a hemispherically shaped welded tip at one end and adapted at a second end to a vacuum fitting for connection to the measurement device.

In another aspect of the invention, the membrane material which is used to at least partially fill the pore formed in the probe tip is silicone.

In yet another aspect of the invention, the probe has a plurality of pores. These pores are formed proximate the probe tip in the end, or the side walls, or both, of the steel tubing, and are spaced apart from one another by a predetermined distance.

The present invention is also directed to a method for constructing a gas measurement probe for measuring gas tensions comprising the following steps: sealing a hollow tubing at one end with a solid tip, forming at least one pore at a predetermined location on said solid tip, inducing a vacuum in the tubing such that a gas leak enters the tubing at said pore, sealing said pore upon the achievement of a desired leak rate with a membrane material such that only low molecular weight gases permeate said membrane.

The pore in the probe permits the entry of extremely small samples of low molecular weight gases, such as $O_2$, $CO_2$, methane, acetone, and alcohols, into the mass spectrometer system. The probe tip can therefore be miniaturized so that measurements can be taken inside arterioles and venules. These and other features of the present invention will become clear from the following detailed description and claims appended thereto.

Thus, the present invention provides an extremely low gas sample rate to measure liquid phase gas tensions. The gas sample rate is of such a low level, that there is minimal diffusional resistance in the liquid layer. All of the diffusional resistance lies within the membrane itself, and the probe is not sensitive to changes in liquid stirring, thus making the measurements more quantitative. Also, the low gas sample rate allowed by a device in accordance with the present invention permits gas tension measurements appearing in very small blood samples.

DETAILED DESCRIPTION OF THE PRESENT INVENTION

The present invention is described with reference to the enclosed Figures wherein the same numbers are utilized where applicable. The present invention is directed to a system which couples a novel membrane inlet probe 14 with a mass spectrometer 12 in such a way as to permit measurement of partial pressures of low molecular weight, non-polar gases in liquids, such as those found in blood or saline. Although the preferred embodiment shows a mass spectrometer, it must be kept in mind that other measurement devices, such as gas chromatographs, infrared spectrometers, Raman spectrometers, and the like, may also be used in conjunction with a probe in accordance with of the present invention.

A key feature of the present invention is the provision of an extremely low sampling rate that is required to measure the liquid phase gas tensions. By using very low sample rates, the mass spectrometer probe of the present invention does not induce any significant diffusional resistance in the liquid. The present system eliminates the difficult problem of calibration of membrane inlet systems in situ.

In accordance with the preferred embodiment, the present invention includes a mass spectrometer 12 which preferably includes a quadruple type of mass spectrometer (UTI 100 C) that is designed for moderate resolution and very high sensitivity. In a preferred embodiment, this mass spectrometer is housed in an all metal vacuum system with tandem thermomolecular and ion pumps 16, 18.

The probe 14 of the present invention is highly useful as a research tool to make perivascular measurements of gas tensions ($O_2$, $CO_2$, $H_e$, Xenon) in saline perfusate in a vital microscopy preparation. The novel probe 14 of the present invention is now described with reference to FIGS. 2–5. In principle, the probe 14 of the present invention could be connected to any mass spectrometer or other gas measurement device. For example, very low gas sampling typically requires a mass spectrometer system that includes an electron multiplier, housed in a vacuum system, which is capable of very high temperature and high vacuum bake-out cycles.

The probe of the present invention is now described in detail. Initially, the probe 14 is constructed from a metal such as a specially welded metal stainless steel tubing 20. The probe 14, in a preferred embodiment, comprises a cylindrical hollow tubing 20. It is to be appreciated that while the tubing 20, in a preferred embodiment, is shown as being constructed from stainless steel and having a cylindrical cross-section, it may also be constructed of numerous alternative metals and alloys, or glass, and may have other cross-sectional shapes. The tip of the probe 14a is welded so as to form a seal.

In a preferred embodiment, the sealed probe tip 14a is hemispherical in shape and the cross-sectional wall thickness of the tip is preferably constant throughout the weld 14c. It is to be appreciated that while the shape of the probe tip 14a has been disclosed as having a hemispherical shape, the probe tip 14a may comprise other geometric shapes and configurations.

The second end of the probe 14b is soldered to an ultra-high vacuum fitting 22, which is then connected via hosing 25 to the mass spectrometer system. The fitting 22 provides a hermetical seal with the spectrometer 12.

A leak or pore 24 is then cut into a spot on the uniform welded probe tip 14a. One way to form the leak or pore 24 is to carefully file the tip of the probe 14a while inducing a vacuum in the probe and monitoring the gas leak rate into the mass spectrometer 12. When a desired leak rate is achieved, the leak or pore 24 is sealed with a porous polymer 26. Though shown in FIG. 2 to occupy the entire thickness of the pore, it should be noted that a membrane 26 need not necessarily do so, depending on the properties of the membrane. Instead of filing, the leak or pore may be laser drilled or micromachined to a predetermined diameter.

Figure 9:
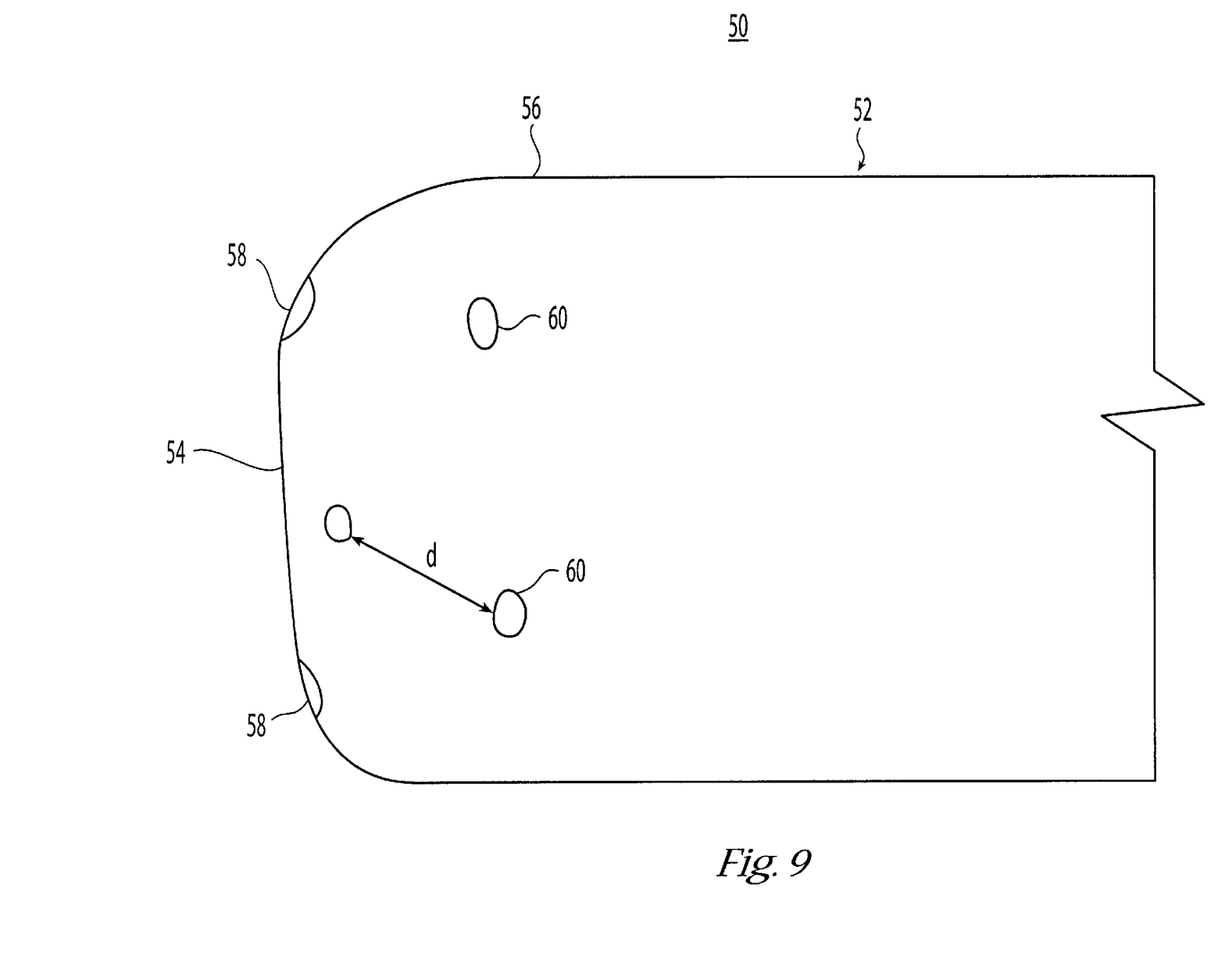
FIG. 9 shows an alternative embodiment of the pore arrangement in a probe of the present invention.

FIG. 9 shows an alternate embodiment of the pore arrangement in a probe 50. The probe 50 is preferably formed from a stainless steel cannula or tube 52 that is $\frac{1}{16}$" in diameter. The tube is provided with an end portion 54. The end portion may be a smoothly rounded surface, as shown in FIG. 9, or a hemispherical cap as discussed above, or even a flat surface formed on the end of the tube 52. A plurality of pores 58, 60 are provided on the probe 50. As shown in FIG. 9, pores 58 may be formed on the end portion 54 and additional pores 60 may be formed on the substantially cylindrical side wall 56 of the tube 52, adjacent to the end portion 54. Also, one may provide pores only on one of the end portion 54 and the side wall 56. The number of pores formed on the tube can be varied. This number depends on such factors as the diameter of the pores, the desired spacing between pores, the size of the probe tip, the diameter of the tubing and other factors affecting the available surface area on which to form the pores.

Preferably, when a multiplicity of pores are used, they are on the order of 15–60 $\mu$m in diameter, and are more preferably 20–30 $\mu$m. To ensure that the pores act independently of one another, the pores should be spaced apart from one another by a distance d of at least 5 pore diameters. More preferably, however, the pores are spaced apart from one another by between 5 and 15 pore diameters. With multiple independent pores, the benefits of rapid time response and low stirring effect are retained, while sensitivity increases linearly with the number of pores. Computer controlled laser drilling and micromachining techniques can be used to form multiple pores at predetermined locations in the tube 52, both in the side wall and in the end portion.

In a preferred embodiment, the porous polymer 26 comprises a very low vapor pressure PTFE (teflon) that functions as a "membrane" in order to keep water out of the mass spectrometer system, while admitting low molecular weight gases into the system. Another preferred material for a porous polymer membrane material is a polymeric grease such as KRYTOX®. The KRYTOX® provides a linear gas sample rate with respect to outside gas pressure. Typically, the porous polymer can be manually wiped onto the tip of the probe to at least partially fill the pore with the polymer. Any excess polymer can also be manually wiped off by hand.

In a most preferred embodiment, silicone, such as that found in common household and industrial silicone sealants, can be used for the membrane. Tests have shown that silicone is far more permeable than the other materials, and therefore results in a probe with increased sensitivity. The silicone can be squeezed from a tube and manually applied, as described above. More precise, automated silicone application procedures can be used, especially when the pores are laser drilled or micromachined.

It is to be noted, however, that the pore may be filled with other materials such as PTFE, polyethylene, polypropylene or any water impermeable polymer which may be formed into a paste, packed and cured. Further, the material can be selected to enhance the permeation of specific gases such as sulfur hexafluoride, diethyl ether, or acetone.

The material which fills the pores need not necessarily be thick enough to extend through the entire thickness of the pore. What is important is that the pore material serve as a barrier to the flow of liquid, but still allow the passage of the gas being measured. It is also important that a pore not be too large, as then it becomes difficult to ensure that the membrane stays in the pore and forms an effective barrier.

It is to be noted that the spatial resolution of the probe is primarily a function of membrane area, which for the probe of the present invention is determined by the diameter of the polymer-filled pore. Because sample flux is directly related to membrane area, reductions in membrane area proportionately reduce the mass spectrometer signal for a given gas partial pressure in the aqueous solution. The theoretical limitation to membrane area, then, is determined by the signal to noise ratio of the mass spectrometer at low sample rates. Modern residual gas analyzers, typically those which use large aperture quadrupole mass filters, electron multipliers, and open grid, long pathlength EI ionization, are sufficiently sensitive that they do not usually limit the ultimate membrane area.

The quality of the vacuum system enclosing the mass spectrometer of the present invention is also important. The presence of substantial vacuum system background at the mass/charge ratios of interest provide a lower limit for measured current, which in turn can prevent realization of the maximum sensitivity of the instrument.

It is to be noted that reductions in vacuum system outgassing rates relative to sample flux rates are especially important for respiratory gases (oxygen and carbon dioxide) and argon, which tend to maintain substantial background peaks after atmospheric venting. Several physiologically inert gases (e.g., helium, SF6, Xe, Kr), by contrast, tend to show little interference from vacuum system background even after atmospheric venting, and in general also have little spectral overlap at their parent mass/charge peaks. In the present invention proper results are achieved by the avoidance of polymers in the vacuum system, tandem turbomolecular and ion vacuum pumping, reduction of the size of the vacuum housing as much as physically feasible, and high temperature baking for 2–3 weeks after each atmosphere exposure. A low vacuum system background also permits increased ionization efficiency by the very simple maneuver of choking the high vacuum pump (throttling) during the measurements, which directs each uncharged molecule through the ion source several times. In addition to limits in basic mass spectrometer sensitivity, reduced membrane area also depends on the practical matter of creating a small pore and filling it with membrane material 26, and producing a leak tight seal around the edges.

Effective membrane area 26 cannot be accurately determined without an accurate measurement of gas sample rate. The limiting factor in the accuracy of the calculation is an estimate of ionization efficiency for the EI source. However, usual estimates of efficiency for EI ionization range from 0.0001 to 0.001. Assuming the use of an open grid, long pathlength electron impact ion source operates at the upper end of this range, we can calculate that a measured current for argon of $10^{-14}$ A corresponds to an argon sample rate of $4.9 \times 10^{-10}$ ml (STP) /min (assuming 100% efficiency for the mass filter, and with corrections for the EM gain supplied by the manufacturer). The membrane thickness, as estimated from time response data, is about 7 microns.

Permeability data for argon in KRYTOX® have not been reported, but it is assumed that values for diffusivity of argon in high density polyethylene ($0.116 \times 10^{-6}$ cm$^2$/sec) and solubility of argon in high density polyethylene (0.010 ml (STP) /cm$^3$-atm) will provide reasonable approximations.

Membrane area can then be estimated as $4.9 \times 10^{-6}$ cm$^2$ from $$A = \frac{Q \cdot \delta}{P \cdot a \cdot D}$$

where Q is the gas sample rate, $\delta$ is the membrane thickness, P is the argon partial pressure in the analyte, a is the solubility of argon in the membrane, and D is the diffusivity of argon in the membrane. Assuming a cylindrical pore geometry, this gives an estimate of 25 microns for the pore diameter.

The flat metal surface of roughly 800 microns that surrounds the pore 24 and its membrane obviously impedes gas flux in the vicinity of the pore and potentially can play a role in limiting spatial resolution for measurement of tissue gas tensions. However, in many cases the appropriate boundary condition for measurement of gas tensions at the tissue surface is zero flux, in which case the flat metal surface is advantageous.

A metal, such as stainless steel, which is used for a probe tip, has a three-dimensional crystalline structure characterized by grain boundaries having a network of channels formed therebetween. Collectively, these channels can form a path from one portion of the metal to another. In a sheet of metal that is 150 $\mu$m thick, these channels can effectively form a path through the thickness of the metal sheet. By filing a portion the outer surface of the probe tip, one can remove any oxide film which has formed on the surface, and open up a path, i.e., a "pore". As explained above, a vacuum induced is induced in the probe and the gas leak rate through the pore is monitored so as to obtain a desired leak rate. A pore formed by this filing technique typically has a diameter of roughly 25 $\mu$m at the filed surface. That portion of the pore closest to the filed surface is then filled with the membrane material. The thickness of the membrane is preferably on the order of 4 to 10 $\mu$m, and more preferably about 6.5–7.5 $\mu$m. Thus, the membrane only fills up a fraction of the depth of the pore. However, the 25 $\mu$m pore diameter and the 7 $\mu$m membrane thickness are consistent with the defect at the grain boundary between crystals in the weld.

Figure 13:
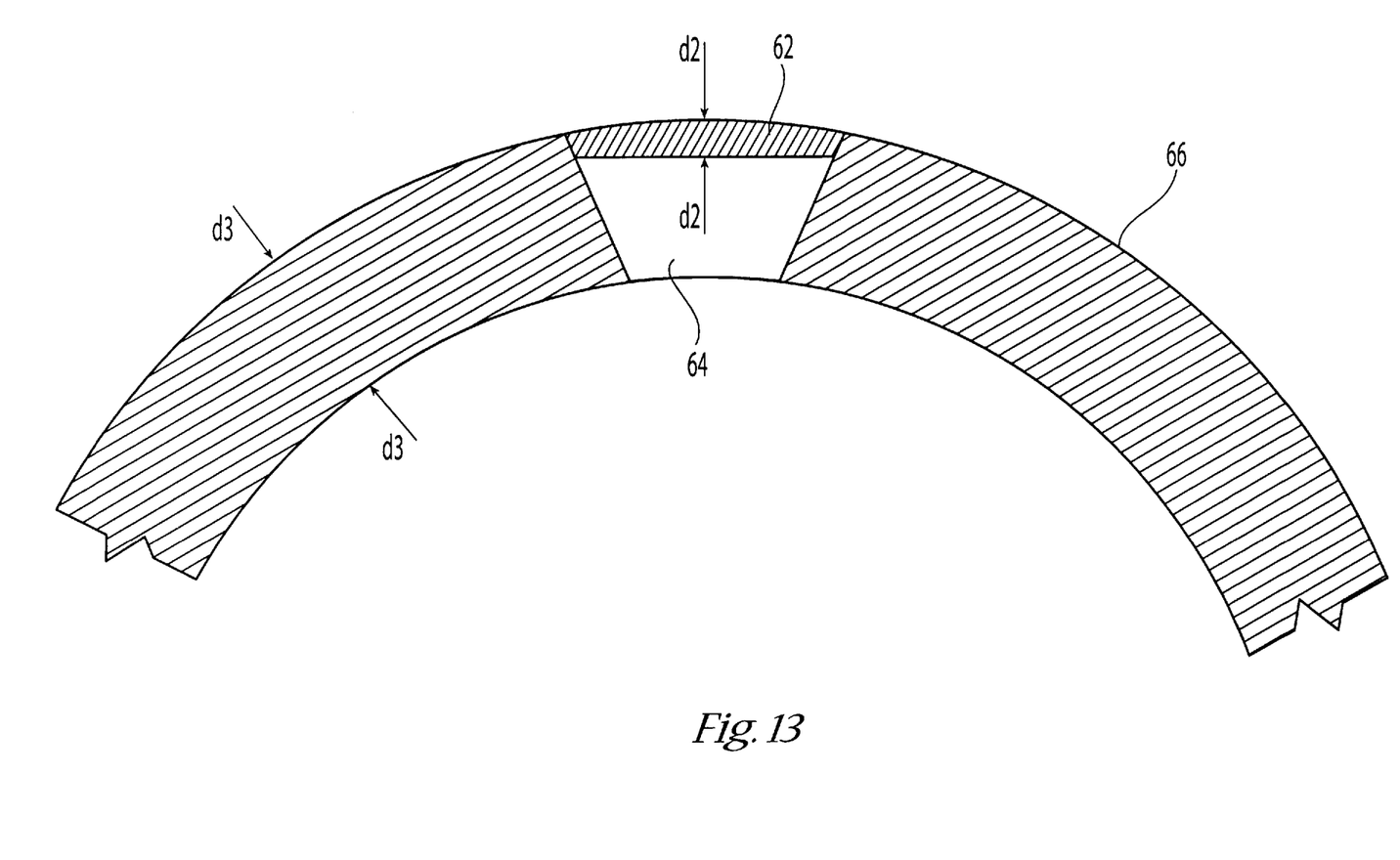
FIG. 13 illustrates the membrane in a conical pore.

The number of pores in not critical and can range from 1 to as many as 300 or even 500, depending on pore size, pore spacing and the size of the probe tip. For more precise pore positioning and formation, and also for the formation of large numbers of pores, say, 20–200 pores in a relatively small surface area, laser drilling or micromachining techniques may be used. Such techniques may be used to form probes having tapered, or even conical sidewalls, so that greater membrane surface area can be provided on the liquid-side, than on the carrier gas-side. Again, as with the pore formed by filing, and as illustrated in FIG. 13, the membrane 62 thickness $d_2$ fills only a fraction of the depth of a pore 64, which extends through a 150 $\mu$m thickness $d_3$ of a metal sheet 66.

As is known by those skilled in the art, stirring effect, or stirring artifact, refers to the difference between the calibration factors for gas tension measured in an unstirred liquid versus agitated liquid. Stirring effect can be minimized by maximizing the membrane diffusional resistance relative to the diffusional resistance in the liquid medium, and is quantified by the ratio of output signals (at identical gas tensions) in still and stirred liquid.

Membrane diffusional resistance is directly proportional to membrane thickness and inversely proportional to the product of gas solubility and gas diffusivity in the membrane. As membrane diffusional resistance is increased to minimize stirring artifact (either by choice of less permeable polymers or thicker membranes), the gas sample rate for a given gas tension decreases proportionately, and the ultimate limit to minimal stirring effect is therefore a function of the signal to noise ratio at low gas sample rates. The role of vacuum system background in limiting ultimate instrument sensitivity for respiratory gases is discussed above.

Figure 7:
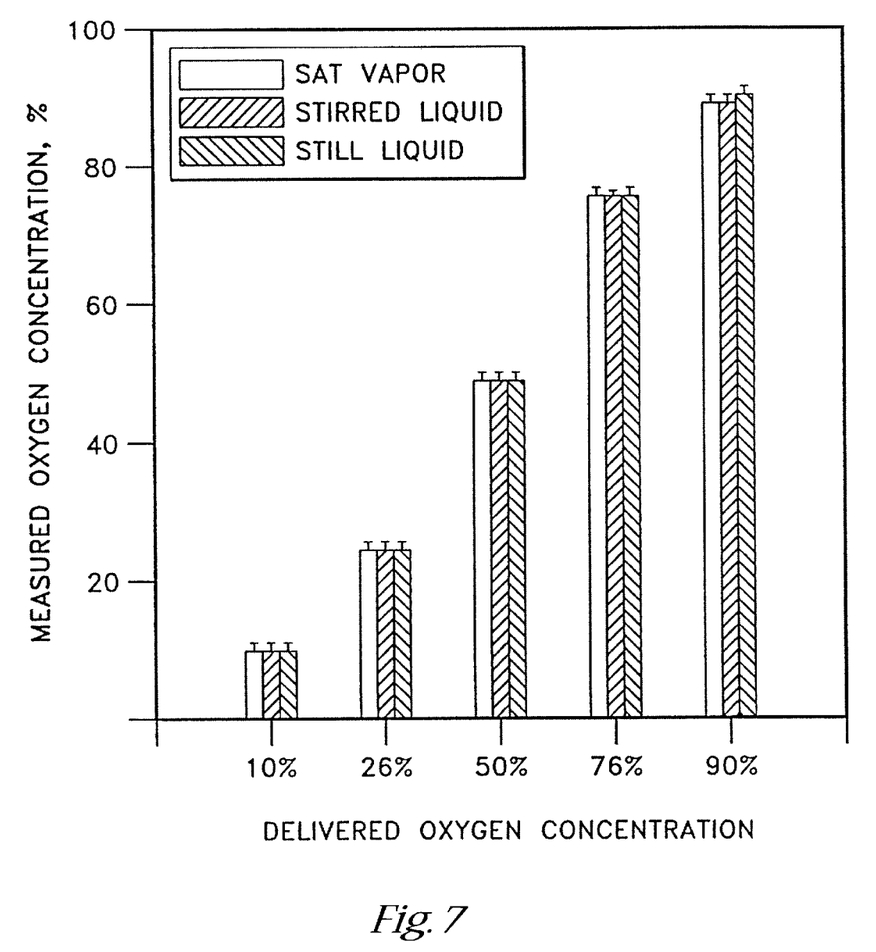
FIGS. 7–8 are graphical representations of oxygen and helium stirring effect, respectively.
Figure 8:
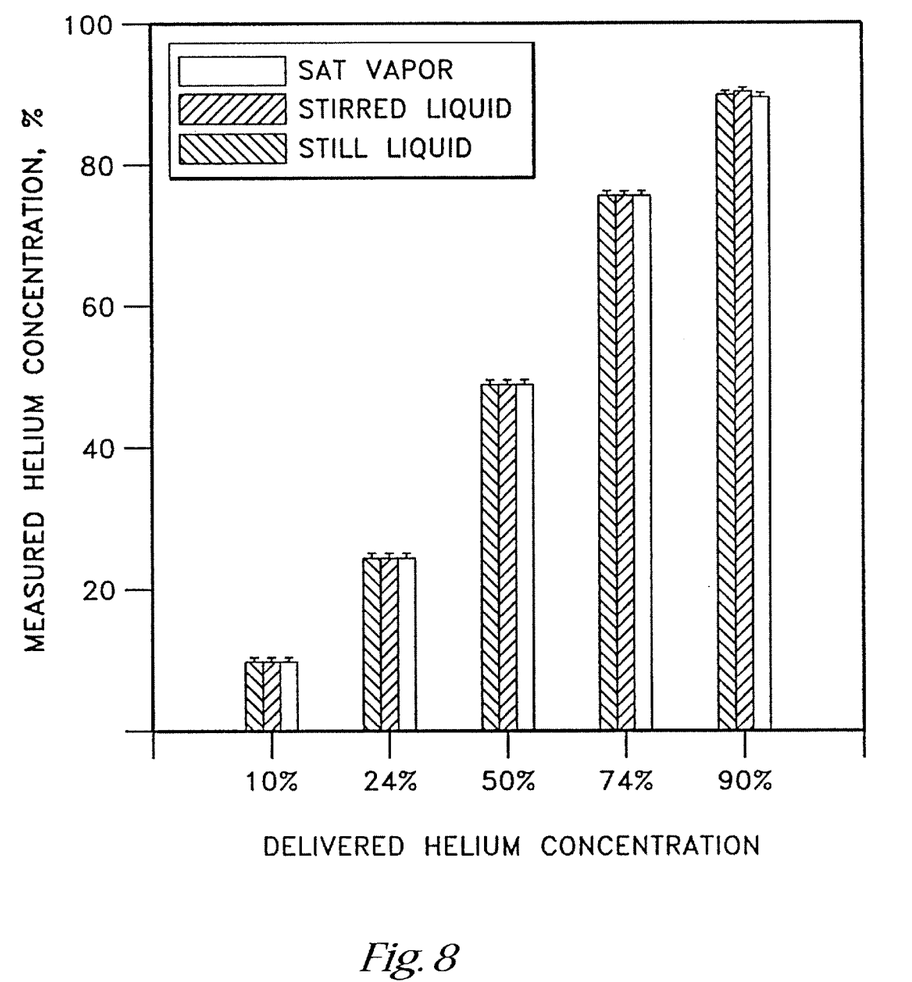

FIGS. 7–8 illustrate the negligible stirring effect in the present invention. The insoluble gases such as helium and SF$_6$, which are predicted to have a larger stirring artifact than the soluble gases, show a difference between still and agitated liquid of less than 1%, and the more soluble gases, such as oxygen, show an undetectable stirring artifact. Negligible stirring effect is advantageous for tissue surface gas tension measurements, because the measurement system calibration becomes independent of the local flow velocity.

In most in-vivo applications, for example the measurement of tissue surface gas tensions within a layer of superfusate covering the tissue, the local flow velocity is unknown. For other applications, in which bulk fluid is sampled and pumped across the membrane (such as measurement of gas tensions in discrete blood samples), the flow velocity can be controlled, but typically the resistance in the blood layer increases as proteins adhere to the membrane surface. In this case, small stirring artifact will reduce the need for frequent recalibration. In addition, flow rates of a sampled fluid can be reduced when stirring effect is small, and therefore blood sample volume can be minimized.

A rapid time response for measurements of gas tensions in aqueous media will be advantageous for many applications, such as the measurement of tissue gas tensions in vivo, and experimental study of reaction kinetics in biochemical fermentation reactors. The time response associated with diffusion through the membrane usually dominates the overall time response for MIMS. For the simple one dimensional geometry of a planar sheet of membrane, the time dependent increase in membrane flux has been shown to be $$\frac{Q_t}{Q_{ss}} = 1 + 2 \cdot \sum_{n=1}^{\infty} (-1)^n \cdot e^{-\left(\frac{n^2 \cdot x^2 \cdot D \cdot t}{2}\right)}$$

where Qt is the gas sample rate into the mass spectrometer at time t, $Q_{ss}$ is the steady state gas sample rate, $\delta$ is the membrane thickness, and D is the diffusivity of the gas in the membrane.

The time required for flux to reach 50% of its steady state value is then $$t_{50} = \frac{\delta^2}{7 \cdot D}$$

emphasizing the crucial role of membrane thickness in determining membrane time response. The small size of the pore makes it physically possible to achieve a very thin membrane and a rapid time response. The membrane thickness can be estimated by applying equation (3) (assuming that the one dimensional case provides a reasonable approximation for the solution for a cylindrical pore) to the time response data for argon.

For a 50% response time of 600 msec and a diffusivity for argon in high density polyethylene (taken as an approximation of the diffusivity in KRYTOX®) of $0.116 \times 10^{-6}$ cm$^2$/sec, an effective membrane thickness of about 7 microns is estimated.

As membrane thickness is reduced to improve response speed, the gas sample rate per unit area of membrane increases, potentially leading to increased stirring effect. The present invention demonstrates that the combination of rapid response speed and minimal stirring effect is possible with a cylindrical membrane 26 within a small pore 24. This unique combination is believed to be the result of the three dimensional concentration profiles associated with diffusion through a small pore- the diffusion within the membrane is restricted to one dimension, whereas diffusion gradients within the liquid medium can encompass an entire hemisphere surrounding the pore 24, with the result that the effective area for diffusion in the medium can be much larger than the area for diffusion within the pore 24. This in turn reduces the diffusional resistance within the medium relative to the diffusional resistance of the membrane, resulting in a small stirring artifact despite a thin (and fast) membrane.

Figure 6:
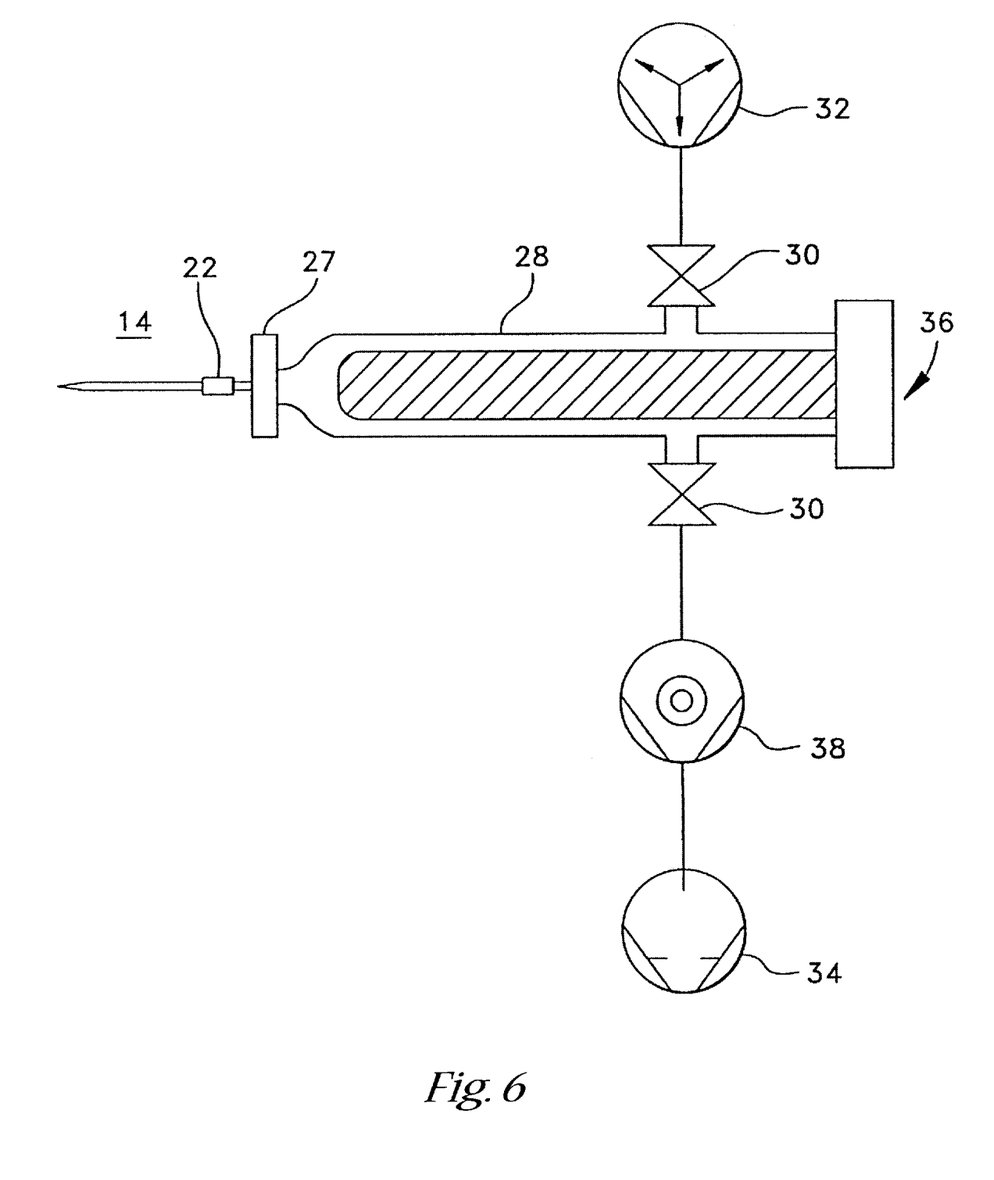
FIG. 6 is shows the probe in conjunction with a gas analysis device.

A more comprehensive embodiment of the present invention is shown in FIG. 6. FIG. 6 illustrates an embodiment including the probe 14 of the present invention affixed to a VCR fitting. The VCR fitting attaches to a 2¾ Cf adapter 27. The adapter is affixed to a custom fabricated vacuum chamber 28 such as manufactured by MDC. The vacuum chamber 28 is connected to two Varian all metal isolation valves 30 such as model No. 951-5027. The invention utilizes pumps 32, 34, 38; an ion pump 32 such as the model NP-020 manufactured by Termionics Laboratory, Inc. and a rotary vacuum pump 34 such as the model D8A by Leybold-Heraeus and a turbo molecular pump such as the Leybold-Heraeus Turbovac 150 38. A UTI quadrupole mass spectrometer 36 is mounted to the vacuum chamber with ion source, quadrupole filter and electron multiplier.

Figure 1:
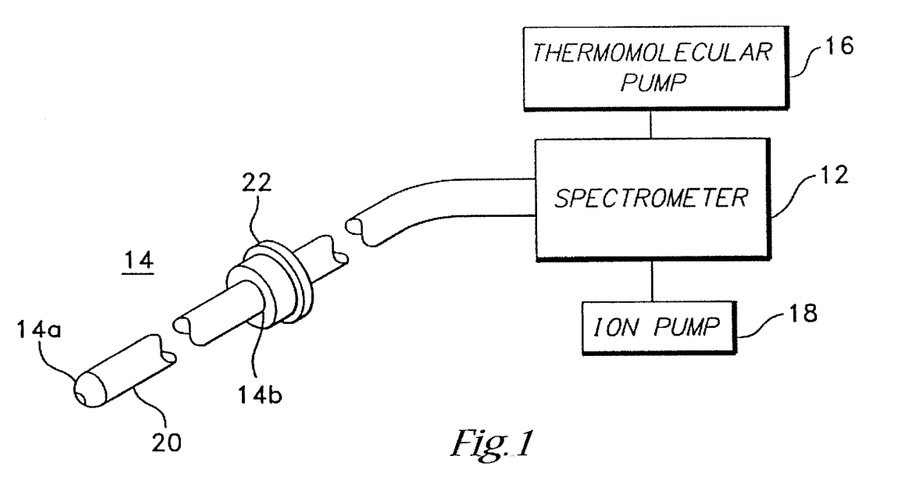
FIG. 1 is a block diagram of the system which utilizes the probe of the present invention in conjunction with a gas measurement device.
Figure 2:
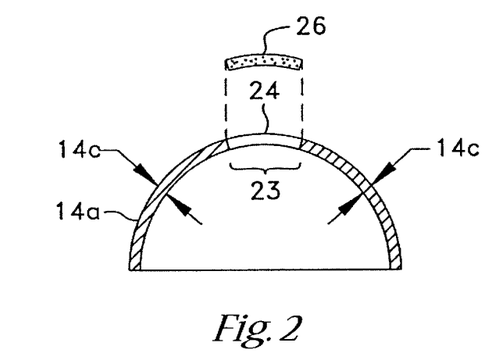
FIG. 2 is a side perspective view of a probe and membrane in accordance with the present invention.
Figure 3:
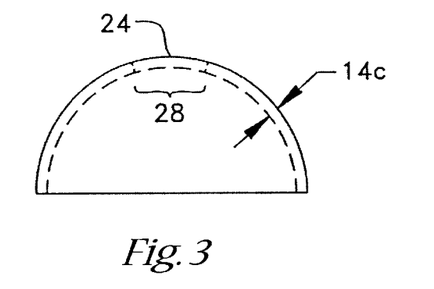
FIG. 3 is a side view of the probe in accordance with the present invention.
Figures 4, 5:
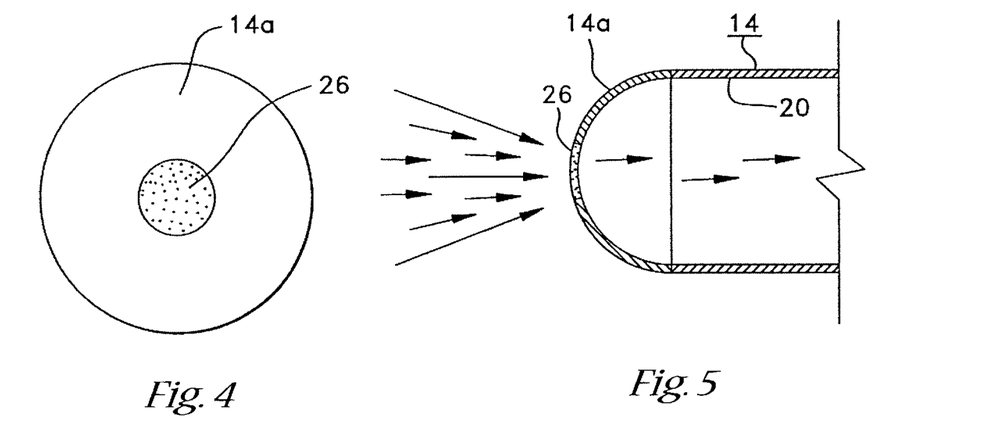
FIG. 4 is an overhead view of the probe and membrane of the present invention.
FIG. 5 is an operational example of the probe and membrane of the present invention.

An operational example of the present invention is now shown with reference to FIG. 5. This operation example assumes that the probe 14 is attached to the mass spectrometer such that a vacuum is induced within the probe and that gases are drawn into the probe via the membrane 26. As shown in FIG. 5, the low sample rate of the probes 14 will lead to minimal disturbance of gas tension profiles and therefore the system can measure not only local gas tensions but also gradients of gas tensions.

An important application of the present invention is in the measurement of multiple inert gas tensions in blood samples, both for research and for clinical care of patients. Currently, the multiple inert gas elimination technique (MIGET) has been used to assess lung function in various diseases both at the bench level research setting and in clinical studies. The mass spectrometer probe of the present invention could make the MIGET technique much more convenient and rapid and probably more popular in the clinical care of patients. Furthermore, these probes can measure a large number of low molecular weight gases such as $O_2$, $CO_2$, methane, acetone, and alcohols, in a liquid phase and may have applications in real time process monitoring for biochemical fermentation reactors in industry.

Figure 10:
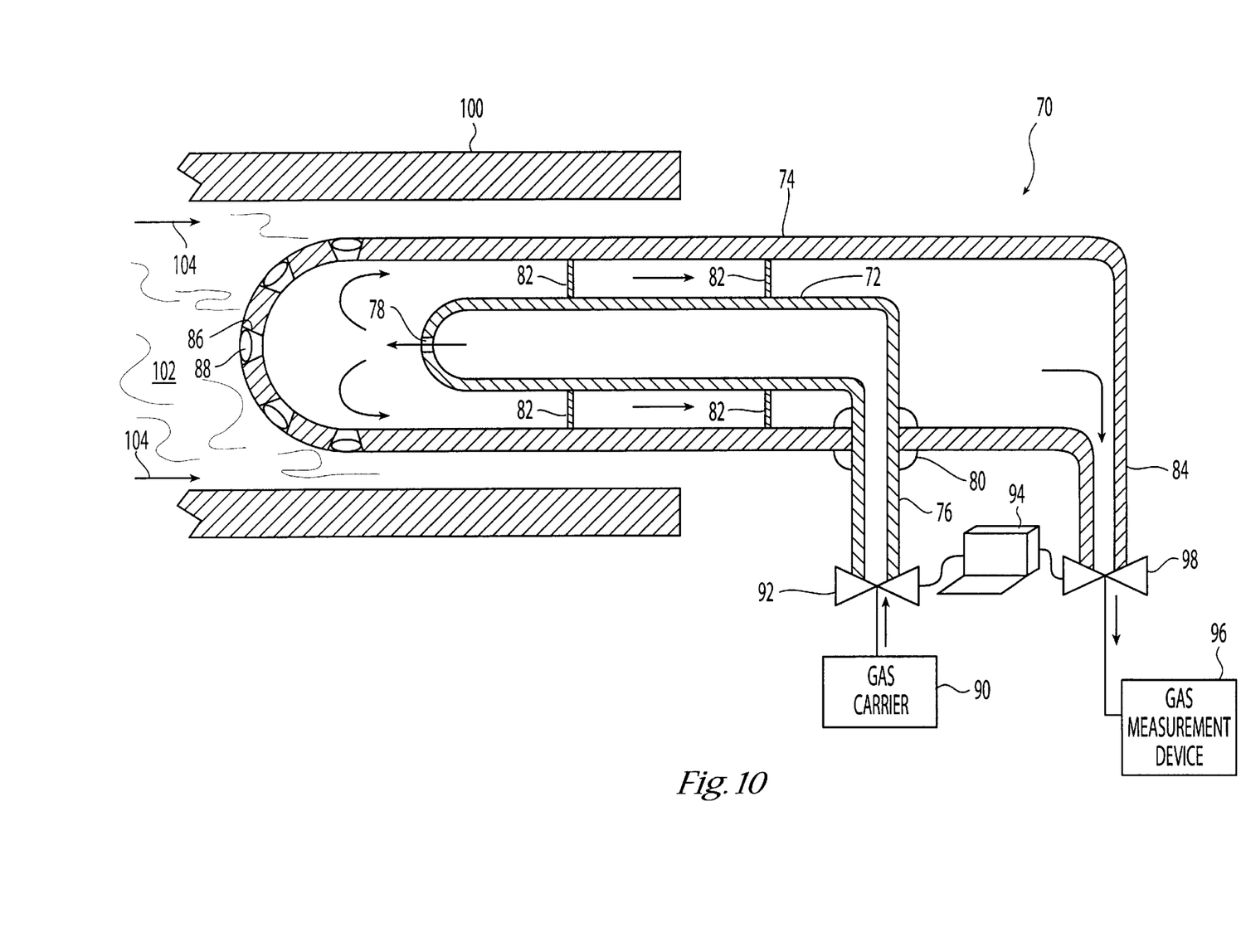
FIGS. 10–11 show another embodiment of a probe in accordance with the present invention.
Figure 11:
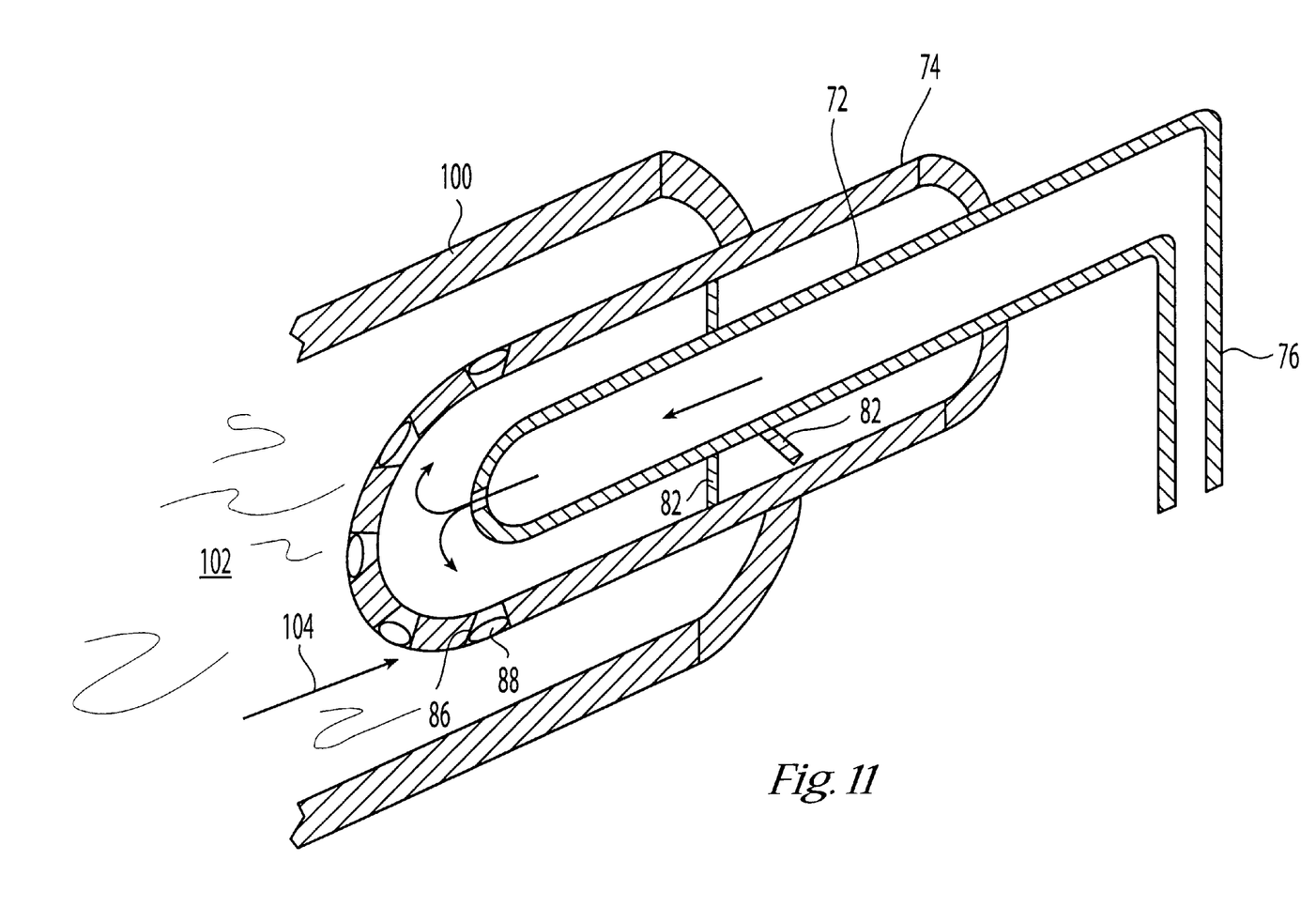

FIGS. 10 and 11 show another embodiment of a probe 70 in accordance with the present invention. The probe 70 comprises an inner tube 72 and an outer tube 74. The inner and outer tubes are preferably formed from stainless steel, ceramic, glass or other material which does not react with gases and fluids of the sort encountered by the probe.

A first end of the inner tube 72 is provided with an inlet duct 76, while its second end is provided with an opening 78. The inlet duct 76 passes through a wall of the outer tube 74 with a gas-tight O-ring seal 80, or equivalent, provided to prevent leaks between the two tubes. The opening 78 formed at the second end of the inner tube is shaped and sized to permit a carrier gas to pass therethrough. A plurality of support struts 82 provided along the length of the inner tube help retain the inner tube 72 within the outer tube 74, and also help maintain a predetermined spacing between the two tubes. The support struts are welded to the outer wall of the inner tube and also to the inner wall of the outer tube, although other joining means may also be used.

At a first end thereof, the outer tube 74 is provided with an outlet duct 84 which is configured shaped and sized for removal of gases which have been introduced into probe 72 via inlet duct 76. At its second end, the outer tube 74 is provided with a plurality of pores 86 filled, at least in part, with a membrane material 88, such as silicone, all as previously discussed.

During use, the inlet duct 76 of the inner tube 72 is connected to a carrier gas source 90 via a first valve 92 which may be under the control of a computer. Similarly, during use, the outlet duct 84 of the outer tube 74 may be connected to a gas measurement device 96 via a second valve 98 which is also under computer control 94. The gas measurement device 96 may be a mass spectrometer, an IR spectrometer, a gas chromatograph, a Raman spectrometer, or other known device which is commonly used to separate molecules present in a carrier gas. It should be noted that the ducts 76, 80 may also take on other configurations, so long as they serve the purpose of delivering the carrier gas, and removing the carrier gas, respectively. It should also be understood that the actual physical connections between the probe ducts 76 and 84, and the carrier gas and the measurement device, respectively, may include conventional fittings, vacuum arrangements, additional isolation valves, and pumps, of the sort discussed above.

During use, a liquid sample tubing 100 containing a liquid sample 102 to be analyzed, and the pore-end of the probe 70, are brought together. This can be done by either introducing the probe 70 into the tubing 100, or by bringing the tubing towards the pore-end of the probe. In those instances in which the container 100 is brought towards the probe, the tubing may be a sleeve of a syringe and the liquid sample is injected over the pore-end of the probe in the direction indicated by the arrows 104. During use, a carrier gas source 82 is connected via a valve 84 to the inlet duct of the inner tube, and the carrier gas, preferably nitrogen, or some other inert gas, is fed into a first end of the inner tube. The carrier gas travels along the length of the inner tube 72 and exits via the opening 78 as indicated by the arrows. The carrier gas picks up analytes in the liquid sample 102 which diffuse through the pores 86, as explained above. The carrier gas laden with these analytes then passes through the outlet duct 84 and valve 98, from which it proceeds to the gas measurement device 96.

Figure 12:
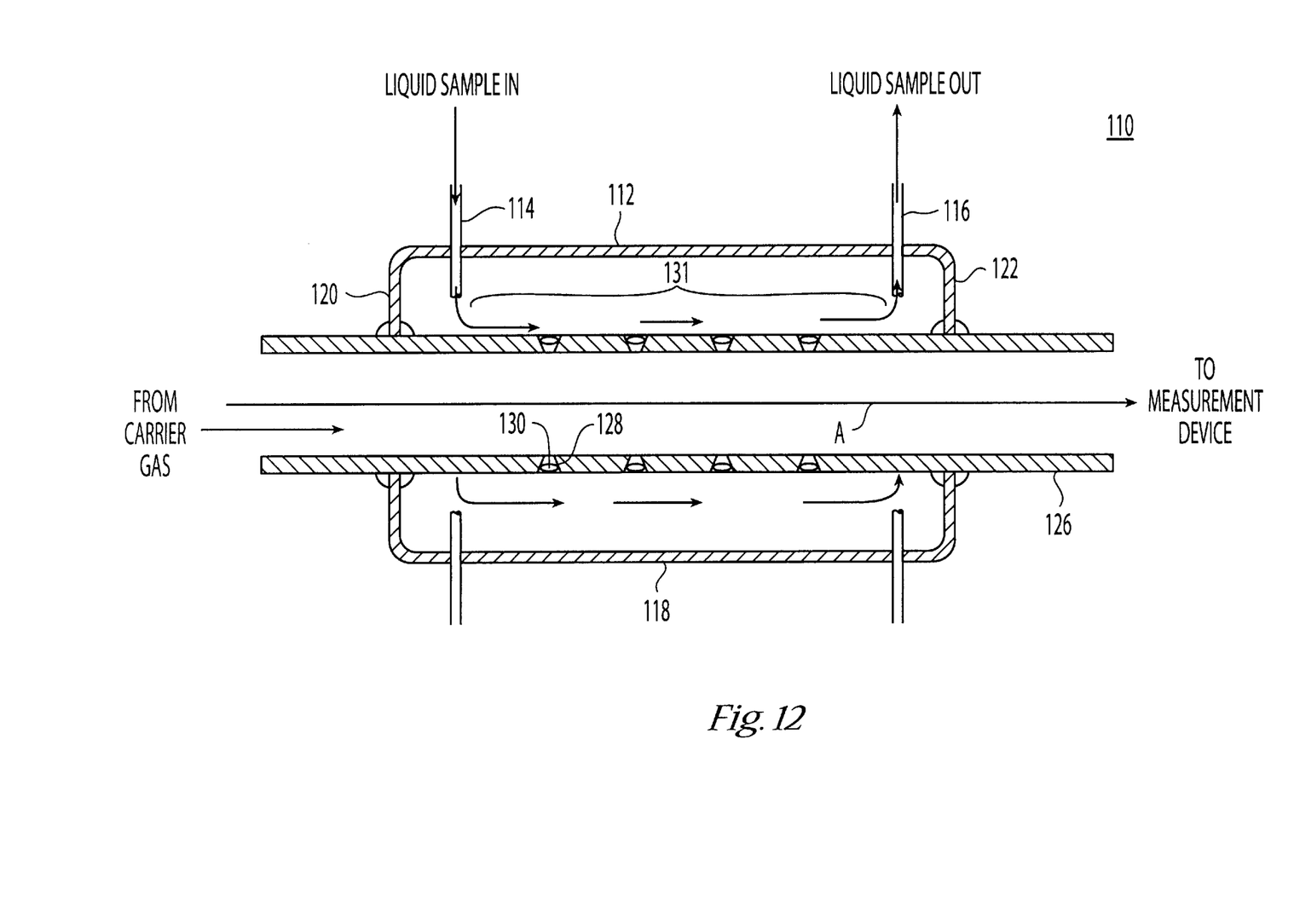
FIG. 12 shows yet another embodiment of a probe in accordance with the present invention.

FIG. 12 shows yet another probe 110 in accordance with the present invention. The probe is preferably a cylindrical container 112 having a sample inlet 114 and a sample outlet 116 connecting to a common chamber 118 housed within the container. The inlet 114 and the outlet 116 are configured for introducing into the chamber, and removing therefrom, a sample liquid, such as blood, as indicated by the arrows. Passing through the first 120 and second ends of the container 112, along its longitudinal axis A, is a carrier tube 126. The carrier tube has a plurality of pores 128, each provided with a membrane material 130, as discussed above. For optimum configuration, the pores 128 are positioned along a first tube portion 131 of the carrier tube, which first tube portion extends between the sample inlet 114 and sample outlet 116. O-ring seals 132 prevent leaks between the container and the sample inlet 114, the sample outlet 116, and the carrier tube 126.

During use, a sample liquid, such as blood, is passed through the chamber defined by the container 112. At the same time, a carrier gas, such a nitrogen, passes through the probe 110 from the first probe end 120 to the second probe end. As the carrier gas passes through the carrier tube 126 that is within the chamber 118, it picks up analytes in the liquid which diffuse through the membranes in the pores. The analyte-laden carrier gas then exits the chamber and is sent on to a gas measurement device, as described before. One advantage of the embodiment of FIG. 12 is that tubing 126 in which the pores and membrane are formed, also serves as the gas carrier tube. However, as is evident from FIG. 12, this probe design also requires a more complicated sample liquid delivery system, and also requires a seal at both ends of the container 112 to prevent any leaks between the carrier gas and the sample liquid within the chamber.

While the probe 110 of FIG. 12 preferably has a cylindrical container, it should be kept in mind that containers of other shapes, such as rectangular or conical may also serve nicely. What is important is that the probe have a chamber into which the liquid sample is introduced, and also a conduit provided with membrane-filled pores through which the carrier gas can pass, the liquid sample coming into contact with the pores, and preferably passing by the pores so as to facilitate diffusion through the membrane.

The present invention has been described with reference to the enclosed Figures. It is to be appreciated that other embodiments fulfill the spirit and scope of the present invention and that the true nature and scope of the present invention is to be determined with reference to the claims appended hereto.

What is claimed is:

1. A gas tension probe comprising a tube having first and second ends, with the first end being sealed and acting as a probe tip, the tip having at least one pore extending therethrough, with said pore being at least partially filled with a membrane that prevents water from entering the tubing and permits low molecular weight gases to enter the tubing by diffusion through the membrane.

2. The gas tension probe of claim 1, wherein the membrane is formed from silicone.

3. The gas tension probe of claim 1, wherein each pore has a diameter between 15–60 $\mu$m.

4. The gas tension probe of claim 1, wherein said probe includes at least 3 pores, each pore being at least partially filled with said membrane.

5. The gas tension probe of claim 4, wherein each pore is spaced apart from its neighboring pores by at least five pore diameters.

6. The gas tension probe of claim 5, wherein each pore has a diameter between 15–60 $\mu$m.

7. The gas tension probe of claim 4, wherein said probe includes at least 20 pores.

8. A gas tension probe comprising:
    an outer tube having a closed first end portion provided with at least one pore extending therethrough, and a second end, and
    an inner tube having a closed first end portion provided with at least one opening formed therein, and a second end, said inner tube being coaxially mounted within said outer tube with said at least one opening being proximate to said at least one pore, wherein
    said at least one pore is at least partially filled with a membrane that prevents water from entering the tubing and permits low molecular weight gases to enter the tubing by diffusion through the membrane.

9. The gas tension probe of claim 8, wherein the first end portion of the outer tube is provided with at least three pores, each of said pores being at least partially filled with said membrane.

10. The gas tension probe of claim 9, wherein each pore is spaced apart from its neighboring pores by at least five pore diameters.

11. The gas tension probe of claim 10, wherein each pore has a diameter between 15–60 $\mu$m.

12. The gas tension probe of claim 8, wherein the membrane is formed from silicone.

13. The gas tension probe of claim 8, wherein the second end of the inner tube is connected to a source of carrier gas, and the second end of the outer tube is connected to a device configured to measure a partial pressure of said carrier gas.

14. A gas tension measurement system comprising:
    a container having a sample inlet through which a liquid may be introduced into a chamber of the container, and a sample outlet through which said liquid may be removed from said chamber, said sample inlet and sample outlet being spaced apart from one another and defining a spacing therebetween; and
    a probe comprising a carrier tube having first and second ends, said carrier tube passing through said chamber and having a first tube portion extending along said spacing, said carrier tube being provided with at least one pore extending therethrough, along said first tube portion, wherein said at least one pore is at least partially filled with a membrane that prevents water from entering the carrier tube and permits low molecular weight gases to enter the carrier tube by diffusion through the membrane.

15. The gas tension measurement system of claim 14, wherein the first tube portion of the carrier tube is provided with at least three pores, each of said pores being at least partially filled with said membrane.

16. The gas tension measurement system of claim 15, wherein each pore is spaced apart from its neighboring pores by at least five pore diameters.

17. The gas tension measurement system of claim 16, wherein each pore has a diameter between 15–60 $\mu$m.

18. The gas tension measurement system of claim 14, wherein the membrane is formed from silicone.

19. The gas tension measurement system of claim 14, wherein the first end of the carrier tube is connected to a source of carrier gas, and the second end of the carrier tube is connected to a device configured to measure a partial pressure of said carrier gas.

* * * * *